United States Patent [19]

Can et al.

[11] Patent Number: 5,766,433
[45] Date of Patent: Jun. 16, 1998

[54] SOLID ELECTROLYTE TYPE GAS SENSOR

[75] Inventors: Zhang Yi Can, Yokohama; Hidekazu Narita, Kuki; Shigeyoshi Kobayashi, Kasukabe; Hidenori Takeuchi, Tatebayashi; Hiroaki Tagawa, Kawasaki; Junichiro Mizusaki, Sendai, all of Japan

[73] Assignees: Akebono Brake Industry Co., Ltd., Tokyo; Akebono Research and Development Centre Ltd., Saitama, both of Japan

[21] Appl. No.: 802,098

[22] Filed: Feb. 19, 1997

[30] Foreign Application Priority Data

| Feb. 22, 1996 | [JP] | Japan | 8-034905 |
| Feb. 29, 1996 | [JP] | Japan | 8-043207 |
| Feb. 29, 1996 | [JP] | Japan | 8-043208 |

[51] Int. Cl.[6] ................................. G01N 27/407
[52] U.S. Cl. ................... 204/424; 204/421; 204/426; 205/784
[58] Field of Search .................. 204/421–426; 429/33, 193; 205/783.5, 784, 784.5

[56] References Cited

U.S. PATENT DOCUMENTS

| 4,042,482 | 8/1977 | Shannon et al. | 429/193 |
| 4,357,215 | 11/1982 | Goodenough et al. | 429/193 |
| 4,507,371 | 3/1985 | Thackeray et al. | 429/193 |
| 5,312,623 | 5/1994 | Plichta et al. | 429/193 |
| 5,449,576 | 9/1995 | Anani | 429/193 |
| 5,451,310 | 9/1995 | Behl et al. | 204/426 |
| 5,492,610 | 2/1996 | Behl et al. | 204/426 |

FOREIGN PATENT DOCUMENTS

| 1-213565 | 8/1989 | Japan . |
| 3-134553 | 6/1991 | Japan . |
| 6-242061 | 9/1994 | Japan . |

*Primary Examiner*—T. Tung
*Attorney, Agent, or Firm*—Morgan, Lewis & Bockius LLP

[57] ABSTRACT

A $CO_2$ gas sensor using a solid reference electrode in combination with a lithium ion conductive solid electrolyte which is at dissociative equilibrium with $CO_2$ gas, characterized in that the solid reference electrode is made of a lithium containing, mixed transition metal oxide conductor which is of the same conduction type as the solid electrolyte. Further, the solid electrolyte comprises a complex carbonate containing $LiAlO_2$ as an aggregate. Furthermore, a mixed electrode is used for the solid-electrolyte type gas sensor, which is prepared by the steps of: mixing a Au powder or paste with a powder of an oxide excluding $Al_2O_3$; rendering a resultant mixture to a paste; applying the paste onto a solid electrolyte; and sintering the applied paste.

6 Claims, 5 Drawing Sheets

SOLID ELECTROLYTE TYPE GAS SENSOR

BACKGROUND OF THE INVENTION

1. Field of the Invention

The present invention relates to a gas sensor that uses a solid electrolyte to measure a $CO_2$ gas level (hereinafter referred to as "a solid-electrolyte type gas sensor" or "a $CO_2$ gas sensor", when applicable).

2. Description of the Conventional Art

With the recent concern over global warming, a growing need for high-performance $CO_2$ gas sensors is realized in a wide range of application including continuous monitoring systems for the $CO_2$ gas level of atmospheric air. Further, $CO_2$ gas senors may be used in control of the environment in residential spaces, greenhouses and biotechnological processes.

The existing $CO_2$ gas sensors operate on various principles such as the absorption of infrared radiations (an optical method of measurement), a wet system (electrolysis), as well as the use of semiconductors and ceramics (e.g., alkali ion conductors and perovskite-type oxides). These principles have their own advantages and limitations and no completely satisfactory $CO_2$ gas sensor has yet been developed.

Under the circumstances, it has been proposed most lately that the $CO_2$ gas level be detected using a solid electrolyte in order to reduce the size and cost of the sensor, facilitate its maintenance and make it portable. As taught in Japanese Patent Publication No. Hei. 3-134553, the proposed method is characterized by combining sodium carbonate with NASICON or $\beta$-$Al_2O_3$ which are each a sodium ion conductor (solid electrolyte) such that a cell is composed as expressed below by (1):

$$CO_2, O_2, Au/Na_2CO_3/NASICON \text{ or } \beta-Al_2O_3/Pt, O_2 \quad (1)$$

The cell (sensor) having this composition generates an electromotive force E as expressed by the following equation (2):

$$E = \Delta G°_{(Na2CO3)}/2F - (RT/2F)\ln(a_{Na2O} \cdot P_{CO2}) \quad (2)$$

where $\Delta G°_{(Na2CO3)}$=standard free energy of formation of sodium carbonate; $a_{Na2O}$=activity of $Na_2O$ in NASICON or $\beta$-$Al_2O_3$; $P_{CO2}$=$CO_2$ partial pressure; R=gas constant; F=Faraday's constant; T=absolute temperature.

This type of sensor determines the $CO_2$ level according to a measured electromotive force, so it requires that the value of $a_{Na2O}$ be constant.

However, the operating temperature of the sensor is as high as 550° C. and above and if it is used for a prolonged period, the value of $a_{Na2O}$ will change gradually causing variations in the electromotive force even at a constant $CO_2$ level. Another problem with the sensor is that if the measurement is conducted in a hot and humid condition, sodium carbonate which is a cell component absorbs moisture and the relationship between $P_{CO2}$ and electromotive force varies so greatly from the case in the dry state that it is impossible to determine the correct $CO_2$ level.

On the other hand, the present inventors also made a study along that line and already proposed a $CO_2$ gas sensor using a solid electrolyte material that had alumina incorporated in a substance comprising lithium carbonate as a principal matrix (Japanese Patent Publication Hei. 6-242061).

However, it was found by experiments that as a result of prolonged heating, the proposed solid electrolyte material experienced a deterioration according to the following scheme:

$$Li_2CO_3 + Al_2O_3 \rightarrow 2LiAlO_2 + CO_2 \quad (3)$$

where the alumina component of the material reacted with the lithium carbonate component to generate lithium aluminate, whereupon the number of interstitial lithium ions capable of moving around in the bulk of the solid electrolyte decreased to such an extent that the ion conductivity of the electrolyte dropped markedly (its electric resistance increased).

As long as the lithium carbonate and the alumina which are two electrolyte components continue to react with each other, the conductivity of the electrolyte will keep decreasing. Since this change increases the internal impedance of the sensor taken as a whole, not only is the specification range of a voltmeter for measuring the output signals of the sensor limited but also the output signals are largely affected by noise.

According to another proposal made in the art, a substance comprising lithium carbonate as a principal matrix was mixed with alumina and subsequently melted. However, the reaction for the generation of lithium aluminate was accompanied by the evolution of $CO_2$ gas, which was incorporated into the melt as it solidified, thereby yielding a porous solid electrolyte. Since the porosity of the solid electrolyte causes the leakage of $CO_2$ gas, the signal output of the sensor will drop unavoidably to thereby deteriorate the precision in gas level detection.

In addition, the aforementioned $CO_2$ gas sensors that uses a solid electrolyte are generally characterized in that a commercial Pt or Au paste is principally used with the electrodes in the $CO_2$ gas detecting portion.

However, most of the $CO_2$ gas sensors of the stated type use a carbonate as the $CO_2$ gas detecting material, so if a commercial Pt paste is used, it forms a compound with the carbonate and the resulting time-dependent change will compromise the long-term stability of the sensor.

A commercial Au paste also has a problem in that it is not inherently intended for use with porous electrodes in gas sensors but emphasis is placed on such design considerations as the density and smoothness that are attained as a result of sintering; therefore, the commercial Au paste is not suitable for use with porous electrodes in gas sensors. That is, the side of the solid electrolyte that contacts the sensitive electrode in the $CO_2$ gas detecting portion is covered with a dense gold film so it has only insufficient contact with the vapor phase to permit a smooth progress of electrode reactions. In addition, the Au paste sinters slowly at the operating temperature of the sensor (300° to 600° C.) until the porosity of the electrode is eventually lost. As a result, the reaction taking place at the interface between the electrode and the solid electrolyte will proceed only with difficulty and the response of the sensor will deteriorate (i.e., prolonged response time).

SUMMARY OF THE INVENTION

An object, therefore, of the present invention is to provide a solid-electrolyte type gas sensor which is improved not only in the precision of sensor's electromotive force but also with respect to the long-term stability and response speed.

Another object of the present invention is to solve the aforementioned problems of the conventional art by preparing a solid electrolyte not from the conventionally used alumina but from lithium aluminate in the form of either a powder or a porous body.

Still another object of the present invention is to solve the aforementioned problems of the conventional art by mixing a Au paste or powder with the powder of NiO or any other oxide that will not react with Au and using the thus prepared electrode material in fabricating a mixed electrode for use with the solid-electrolyte type gas sensor.

According to a first aspect of the invention, there is provided a solid-electrolyte type gas sensor to measure a $CO_2$ gas level comprising: a lithium ion conductive solid electrolyte which is at dissociative equilibrium with $CO_2$ gas; and a solid reference electrode combined with the lithium ion conductive solid electrolyte; wherein the solid reference electrode is made of a lithium containing, mixed transition metal oxide conductor which is of the same conduction type as the solid electrolyte.

According to a second aspect of the invention, there is provided a solid electrolyte material used for a solid-electrolyte type gas sensor to measure a $CO_2$ gas level, comprising: a complex carbonate containing $LiAlO_2$ as an aggregate.

According to a third aspect of the invention, there is provided a mixed electrode used for a solid-electrolyte type gas sensor, which is prepared by the steps of: mixing a Au powder or paste with a powder of an oxide excluding $Al_2O_3$; rendering a resultant mixture to a paste; applying the paste onto a solid electrolyte; and sintering the applied paste.

According to the first aspect of the invention, a lithium ion conductive solid electrolyte is combined with a lithium containing, mixed transition metal oxide conductor of the formula $Li_xMO_y$ (M is a transition metal such as Co, Ni, Fe, Mn, Ti, V or Cr; $0<x\leq 1$; $2\leq y\leq 12$) to make a sensing element and the $CO_2$ level is determined on the basis of the activity of lithium ions in the mixed conductor. If necessary, the lithium containing, mixed transition metal oxide conductor may be mixed with an oxide of the same transition metal. The lithium containing transition metal oxide in the resulting mixture can serve as a lithium reservoir.

According to the second aspect of the invention, the beta-alumina and NASICON which have heretofore been used as principal components of the solid electrolyte are replaced by a lithium aluminate reinforced complex carbonate having a lithium carbonate matrix. This enables the desired solid electrolyte to be prepared easily at temperatures not higher than 1,200° C.; in addition, a $CO_2$ gas sensor using the thus prepared solid electrolyte can be operated at 300° to 400° C. with improved moisture resistance. The $CO_2$ gas sensor finds utility in a wide range of applications including the measurement of $CO_2$ gas level in air atmosphere, control over the environment of residential spaces, agroindustrial processes, the measurement of metabolic functions on bio-surfaces and various medical fields.

According to the third aspect of the invention, the mixed electrode of the invention can maintain the desired porous structure, so the gas to be detected will diffuse smoothly to reach the interface between the electrode and the electrolyte, thereby allowing for a smooth progress of the electrode reaction. In addition, the mixed electrode retains its microstructure in a stable manner over an extended period, which helps not only to prevent the decrease in the response speed of the sensor but also to improve the stability of its response characteristic.

DETAILED DESCRIPTION OF THE PREFERRED EMBODIMENTS

Figure 1:
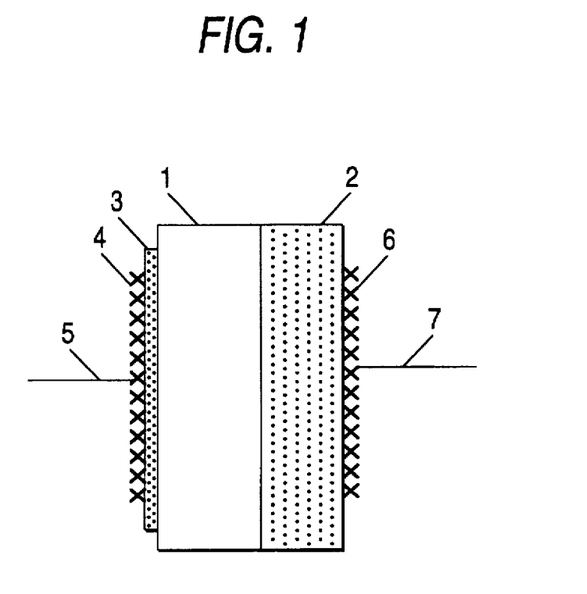
FIG. 1 shows schematically a composition of a solid-electrolyte type gas sensor of the invention.

An first embodiment of the present invention will now be described with reference to the accompanying drawings, in which FIG. 1 shows the concept of a solid-electrolyte type gas sensor according to the present invention, that is, a $CO_2$ gas sensor using cobalt as a transition metal.

Referring to FIG. 1, the gas sensor comprises a solid electrolyte and a solid reference electrode 2. The solid electrolyte 1 comprises 96 wt % of a mixture of 95 mol % $Li_2CO_3/5$ mol % $Li_3PO_4$ and 4 wt % of $LiAlO_2$. The solid reference electrode 2 comprises 95 mol % $LiCoO_2$ and 5 mol % $Co_3O_4$. The two members which are joined together as shown are heated up to 700° C. in a fixed condition such that the solid electrolyte 1 is fused to the solid reference electrode 2 to ensure mutual ion conduction through the junction. A gold (Au) electrode (detecting electrode) 3 in the form of a sintered Au paste is provided on the surface of the solid electrolyte; a gold (Au) screen 4 is placed in contact with the outer surface of the Au electrode 3 and the Au screen in turn is fitted with a Au lead wire 5. Upon sintering, the Au paste turns porous so that it becomes gas permeable. A platinum (Pt) screen 6 is placed in contact with the opposite surface of the solid reference electrode 2 and the Pt screen 6 in turn is fitted with a Pt lead wire 7.

The above-described arrangement provides a cell in which the Au electrode 3 is a cathode and the solid reference electrode 2 is an anode as shown by (4):

$$CO_2, O_2, Au/Li_2CO_3\text{—}Li_3PO_4\text{—}LiAlO_2/LiCoO_2\text{-}5 \text{ mol } \% \ Co_3O_4/Pt \quad (4)$$

Since the Li cations in the solid reference electrode migrate through the solid electrolyte to reach the detecting electrode on which $CO_2$ is present, the following reactions take place at the anode and the cathode, respectively, of the cell:

$$(Anode) \ LiCoO_2 \rightarrow Li_{1-x}CoO_2 + xLi^+ + xe^- \quad (5)$$

$$(Cathode) 2Li^+ + CO_2 + 1/2O_2 + 2e^- \rightarrow Li_2CO_3 \quad (6)$$

Hence, the overall cell reaction is expressed by the following:

$$2LiCoO_2 + xCO_2 + x/2O_2 \rightarrow 2Li_{1-x}CoO_2 + xLi_2CO_3 \quad (7)$$

The electromotive force E of the sensor is given by the following equations:

$$E = E° + (RT/2F)\ln P_{CO_2} + (RT/4F)\ln P_{O_2} \quad (8)$$

$$\begin{aligned}
E° &= ((\mu_{LiCoO_2} - \mu_{Li_{1-x}CoO_2})/ \\
&\quad x + 1/2\mu°_{CO_2} + 1/4\mu°_{O_2} - 1/2\mu°_{Li_2CO_3})F \\
&= (\mu^+_{Li} + 1/2\mu°_{CO_2} + 1/4\mu°_{O_2} - 1/2\mu°_{Li_2CO_3})/F \\
&= (\mu^+_{Li} - \mu°_{Li} + 1/2\Delta G°_{(CO_2)} - 1/2\Delta G°_{(Li_2CO_3)})/F
\end{aligned} \quad (9)$$

where $\mu_{Li}^+$ = chemical potential of lithium ions in $Li_{1-x}CoO_2$; $\mu°_{Li}$ = standard chemical potential of lithium metal.

If $\mu_{Li}^+$ and $P_{O_2}$ (assuming that the sensor is placed in air atmosphere) are kept constant, one can determine the $CO_2$ level of the atmosphere by measuring the electromotive force E of the cell.

Figure 2:
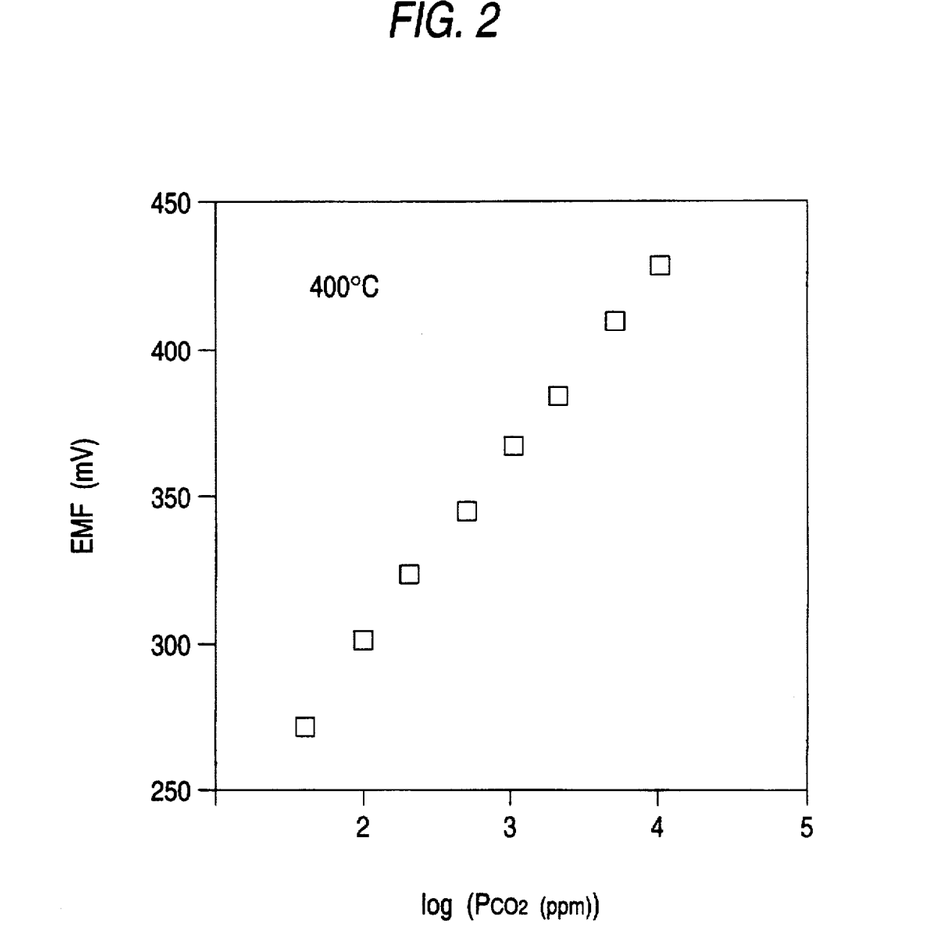
FIG. 2 is a graph showing the electromotive force of the sensor as a function of the $CO_2$ level.

FIG. 2 shows the relationship between the electromotive force of a $CO_2$ gas sensor having the above-described construction and the $CO_2$ level for the case where the sensor was operated by heating at about 400° C. with a heater (not shown). Obviously, the electromotive force of the sensor changes linearly and reproducibly with the $CO_2$ level in accordance with the Nernst equation and, hence, the $CO_2$ level can be determined from the relationship expressed by the Nernst equation.

Figure 3:
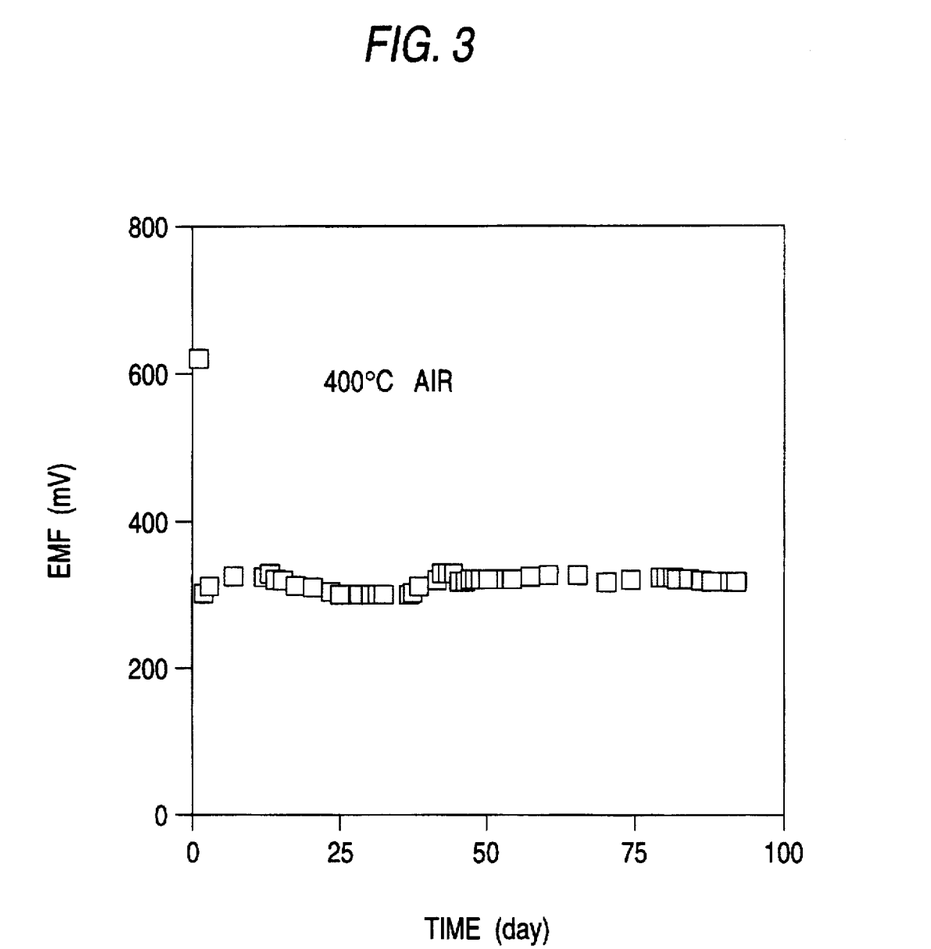
FIG. 3 is a graph showing the operational stability of the sensor with time.

The $CO_2$ gas sensor designed on the above-described principle was operated continuously for an extended period in air atmosphere and the result is shown in FIG. 3, from which one can see that correct and consistent measurements were possible without any time-dependent changes in the output. Experiments were also performed with solid reference electrodes that were made of lithium containing mixed oxide conductors in which transition metals other than Co were employed. The results were the same as that obtained in the case of using Co and, hence, the theory behind the operation of the invention sensor was derived.

An example of the $CO_2$ gas sensor of the present invention will now be described.

A solid electrolyte 1 made of a lithium ion conductor comprising of 96 wt % of a mixture of 95 mol % $Li_2CO_3$/5 mol % $Li_3PO_4$ and 4 wt % of $LiAlO_2$ was joined to a solid reference electrode 2 (95 mol % $LiCoO_2$+5 mol % $Co_3O_4$) and the two members were fused together by heating up to 700° C. A porous Au electrode 3 and a Au screen 4 serving as a current collector were provided on one surface of the solid electrolyte and a Au lead wire 5 was attached to the Au screen 4. The solid reference electrode was provided with a Pt screen (current collector) 6 which, in turn, was fitted with a Pt lead wire 7. The thus constructed sensor was heated to 400° C. and placed in the gas atmosphere to be measured. The $CO_2$ level of the atmosphere was determined by calculation from the electromotive force of the sensor. The heating temperature of the sensor was preferably in the range of 350° to 400° C.

The methods of preparing the solid electrolyte and the solid reference electrode, as well as the process for fabricating a cell using these elements will now be described.

(1) Preparing the Solid Electrolyte:

The case of preparing the solid electrolyte from a lithium ion conductor consisting of 96 wt % of a mixture of 95 mol % $Li_2CO_3$/5 mol % $Li_3PO_4$ and 4 wt % of $LiAlO_2$ is specifically described below. In order to improve the mechanical strength of the solid electrolyte, $LiAlO_2$ nonreactive with $Li_2CO_3$ was added. The powders of $Li_2CO_3$, $Li_3PO_4$ and $LiAlO_2$ were mixed in a mortar in the proportions that would provide the stated composition and the mixture was melted in an alumina crucible at 750° C. The melt was cast into an alumina crucible, solidified and left to cool. The solidified product was ground to prepare a feed powder, which was compressed to a disk having a diameter of 7 mm and a thickness of 2 mm. The disk was sintered at 690° C. for 1 h in air atmosphere to yield the desired solid electrolyte.

(2) Preparing the Solid Reference Electrode:

The solid reference electrode which was a lithium containing, mixed transition metal oxide conductor was prepared from a sinter comprising 95 mol % $LiCoO_2$ and 5 mol % $Co_3O_4$. The $LiCoO_2$ was synthesized by a solid-phase process. Lithium carbonate and basic cobalt carbonate were used as starting materials and weighed in specified molar ratios. The starting materials were then mixed in a mortar together with a small amount of ethanol and the mixture was calcined at 850° C. for 24 h in air. The phase produced in the resulting powder was identified by X-ray diffraction (XRD). After adding $Co_3O_4$ in a specified molar ratio, the resulting powder was compressed to a disk having a diameter of 7 mm and a thickness of 2 mm. The disk was sintered at 950° C. for 4 h in air atmosphere to yield the desired solid reference electrode.

(3) Cell Fabrication:

The specimens prepared by the procedures described in (1) and (2) above were joined together and heated up to 700° C. so that they were fused together. The outer surface of the solid electrolyte was polished smooth and provided with a sintered Au paste to form a detecting electrode.

The above procedures enabled the fabrication of the sensor shown schematically in FIG. 1.

Next, processes for preparing a solid electrolyte for the solid-electrolyte type gas sensor from the lithium aluminate are hereunder described in detail.

(1) Process 1:

Dried powders of $Li_2CO_3$, $Li_3PO_4$ and $LiAlO_2$ (which may be in a fiber form) are mixed. The respective components are weighed in such amounts that $Li_3PO_4$ accounts for 0.5 to 15 wt % of $Li_2CO_3$ and that the $LiAlO_2$ powder (or fiber) accounts for 1 to 60 wt % of the total composition. The mixing is done in an alumina mortar and the resulting mixture is put into an alumina crucible, where it is melted under agitation at 700° to 770° C.; the melt is transferred into a separate ceramic container and allowed to solidify. The solidified product is ground coarsely and then comminuted by known means such as a mortar or mill. The resulting fine powder is compressed and sintered at 670° to 720° C. to produce a pellet of solid electrolyte. The pellet is worked to a desired shape, thereby yielding a sensing element.

(2) Process 2:

A powder mixture of $Li_2CO_3$ and $Li_3PO_4$ which has been adjusted such that $Li_3PO_4$ accounts for 0.5 to 15 wt % of $Li_2CO_3$ is put into an alumina crucible and melted at 700° to 770° C. under agitation. The melt is transferred into a separate ceramic container and allowed to solidify. The solidified product is ground coarsely and then comminuted by known means such as a mortar or mill. The resulting fine powder is mixed with a $LiAlO_2$ powder (or fiber), which has been weighed in an amount that accounts for 1 to 60 wt % of the total composition. The resulting powder mixture is compressed and sintered at 670° to 720° C. to produce a pellet of solid electrolyte. The pellet is worked to a desired shape, thereby yielding a sensing element.

(3) Process 3:

A powder mixture of $Li_2CO_3$ and $Li_3PO_4$ which has been adjusted such that $Li_3PO_4$ accounts for 0.5 to 15 wt % of $Li_2CO_3$ is put into an alumina crucible and melted at 700° to 770° C. under agitation. A preliminarily provided porous body of lithium aluminate (or fiber-reinforced lithium aluminate) is put into the melt. When it has been fully impregnated with the melt, the pellet is taken out of the alumina container and left to cool. The excess carbonate is scraped off the pellet's surface and the pellet is worked to a desired size and shape, thereby yielding a sensing element.

Table 1 lists various formulations for the mixing of $Li_2CO_3$, $Li_3PO_4$ and $LiAlO_2$ in preparing the above-described solid electrolytes.

TABLE 1

| Formulation, wt % | $Li_2CO_3$ | $Li_3PO_4$ | $LiAlO_2$ |
|---|---|---|---|
| Case 1 | 90.00 | 9.00 | 1.00 |
| | 86.36 | 8.64 | 5.00 |
| | 81.82 | 8.18 | 10.00 |
| | 72.72 | 7.28 | 20.00 |
| | 63.63 | 6.37 | 30.00 |
| | 54.54 | 5.46 | 40.00 |
| | 36.36 | 3.64 | 60.00 |
| Case 2 | 94.42 | 4.58 | 1.00 |
| | 90.61 | 4.39 | 5.00 |
| | 85.84 | 4.16 | 10.00 |
| | 81.07 | 3.93 | 15.00 |
| | 76.30 | 3.70 | 20.00 |
| | 57.23 | 2.77 | 40.00 |
| | 38.15 | 1.85 | 60.00 |
| Case 3 | 97.46 | 1.54 | 1.00 |
| | 93.52 | 1.48 | 5.00 |
| | 88.60 | 1.40 | 10.00 |
| | 83.68 | 1.32 | 15.00 |
| | 78.75 | 1.25 | 20.00 |
| | 59.07 | 0.93 | 40.00 |
| | 39.38 | 0.62 | 60.00 |
| Case 4 | 68.14 | 11.86 | 20.00 |

The all formulations in Table 1 satisfy the following conditions: If the respective amount of $Li_2CO_3$, $Li_3PO_4$, $LiAlO_2$ are X, Y, Z, the molar ratio of X:Y is 91–99:9–1 and the weight ratio of (X+Y):Z is 99–40:1–60. In case 1, the molar ratio of X:Y is 95:5 and the weight ratio of (X+Y):Z is 99–40:1–60. In case 2, the molar ratio of X:Y is 97:3 and the weight ratio of (X+Y):Z is 99–40:1–60. In case 3, the molar ratio of X:Y is 99:1 and the weight ratio of (X+Y):Z is 99–40:1–60. In case 4, the molar ratio of X:Y is 91:9 and the weight ratio of (X+Y):Z is 80:20.

The solid electrolytes thus prepared have the following characteristics.

Figure 4:
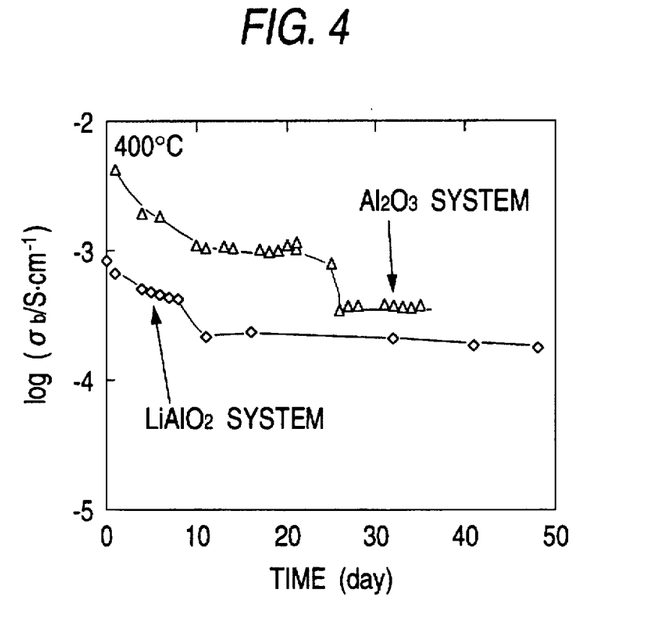
FIG. 4 is a graph in which the conductivity of a solid electrolyte employing lithium aluminate in accordance with the invention is compared with the conductivity of a solid electrolyte using aluminum oxide as in the conventional art.

(A) Instead of the alumina which will react with lithium carbonate, lithium aluminate which is the product of the reaction is mixed with the other starting materials and, hence, the decrease in the number of lithium ions due to the unwanted reaction in the electrolyte (i.e., the problem stated in association with the conventional art) is sufficiently prevented to ensure that the electrolyte will maintain its high conductivity and structure for an extended time period (thereby minimizing the time-dependent change of the electrolyte). FIG. 4 is a graph in which the conductivity of a solid electrolyte employing lithium aluminate in accordance with the invention is compared with the conductivity of a solid electrolyte using aluminum oxide as in the conventional art. Obviously, the solid electrolyte according to the invention experiences less time-dependent change.

(B) The mixing of lithium aluminate rather than alumina eliminates the gas evolution which would otherwise occur due to the reaction with a carbonate during melting under agitation and this contributes to the preparation of a dense solid electrolyte.

(C) The mixing of lithium aluminate has the added advantage of preventing the growth of carbonate crystals and, hence, the formation of gaps between crystals, thereby eliminating the passageways for gas leakage.

(D) Since lithium aluminate is dispersed in the carbonate to a certain degree of uniformity or a porous body of lithium aluminate is impregnated with the carbonate, the lithium aluminate will serve as an aggregate in the prepared solid electrolyte, thereby increasing its mechanical strength while ensuring that the increased mechanical strength is maintained for an extended time period.

In the above three processes for preparing a solid electrolyte, $Li_3PO_4$ is mixed with $LiAlO_2$ as the aggregate. However, it is possible to use a lithium salt having an oxoacid group having a different valence than a carbonate group except for $Li_3PO_4$. For example, $Li_2SO_4$, $LiNO_3$ or the like may be used instead of $Li_3PO_4$.

Further, a carbonate of a metal ion having a different valance than lithium can be further added to the complex carbonate containing $LiAlO_2$ as the aggregate. For example, $CaCO_3$, $BaCO_3$, $SrCO_3$ or the like may be mixed at the initial stage of the aforementioned processes.

Incidentally, the plurality of kinds of the above lithium salts and carbonates may be added.

Next, processes for preparing the mixed electrode of the invention are hereunder described.

A gold (Au) powder having an average particle size of 0.5 to 10 μm, desirably 0.5 to 2 μm, is mixed with a NiO powder having an average particle size of 0.1 to 50 μm, desirably about 0.5 to 20 μm, in such an amount that NiO accounts for 5 to 60 wt % of the Au powder, with ethanol being subsequently added. After thorough mixing, ethanol is evaporated from the mixture. A small amount of a solvent such as turpentine oil or castor oil is added to the residue and mixing is effected to render it to a paste. The paste is then applied onto a solid electrolyte and the applied coat is sintered at about 400° C. or above to fabricate a mixed electrode.

Figure 5:
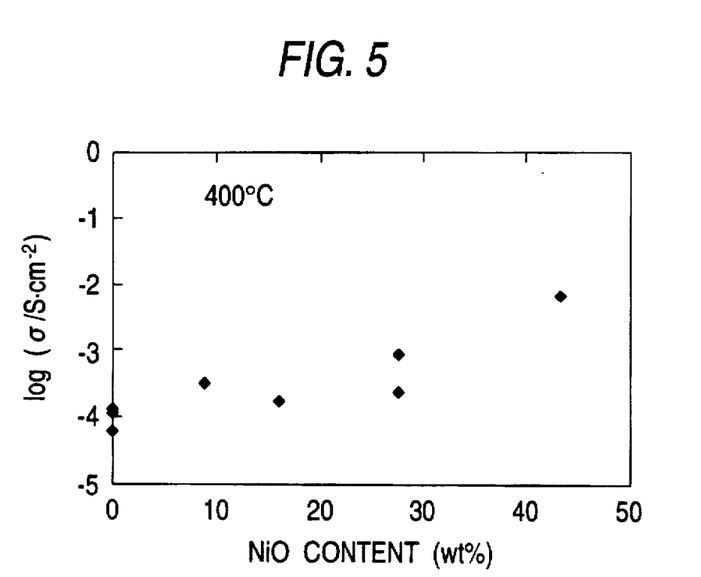
FIG. 5 is a graph showing the relationship between the interfacial conductivity of a Au/NiO mixed electrode and the NiO content.
Figure 6:
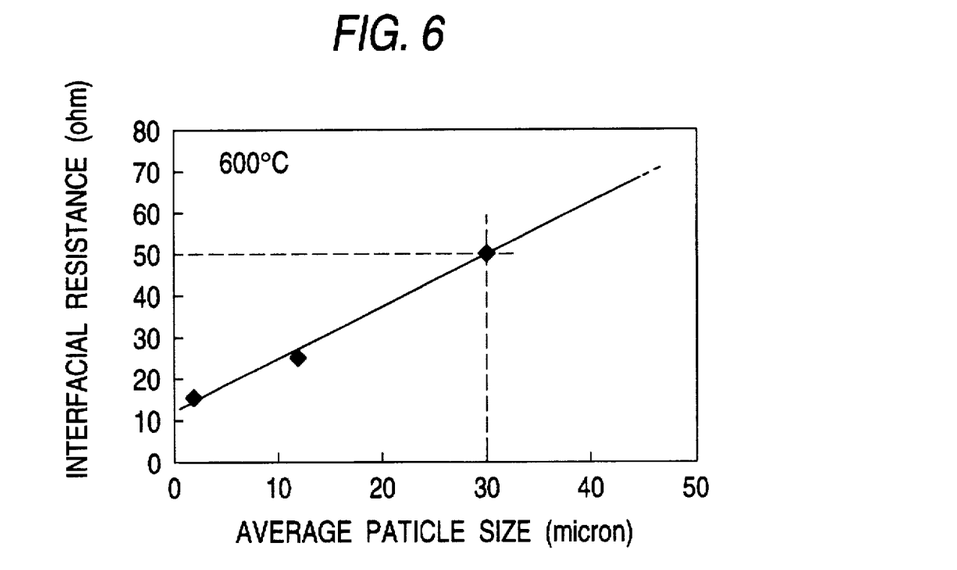
FIG. 6 is a graph showing the relationship between the average particle size of a NiO powder and the interfacial resistance of an electrode using it.

The thus fabricated Au/NiO mixed electrode was measured for interfacial conductivity, which varied with the NiO content as shown in FIG. 5. Obviously, at 400° C., the interfacial conductivity increased (resistance decreased) with the increasing NiO content. The interfacial resistance of the electrode also varies with the average particle size of the NiO powder to be mixed and the smaller the electrode's interfacial resistance, the better (values smaller than 50Ω are desirable); therefore, as typically shown in FIG. 6, the average particle size of the NiO powder is desirably 30 μm and smaller at 600° C.

If, in the case under consideration, the NiO content is so much increased as to cause a significant decrease in the strength of adhesion of the mixed electrode to the solid electrolyte, a glass frit or the like may be added to ensure the required strength. If a glass frit is used, the electrode retains its porosity and yet has the necessary strength of adhesion to the solid electrolyte. In order to ensure that no unwanted reactions will occur between the glass frit and each of the constituent materials such as the electrode and the solid electrolyte, the addition of the glass frit should be as small as possible (preferably not exceeding 10 wt %).

If a paste is to be prepared by the addition of turpentine oil only, it is difficult to adjust the viscosity and fluidity of the paste being prepared and the Au particles are prone to separate from the NiO particles, causing uneven distribution of Au and NiO in the sintered product. In order to eliminate this difficulty, an organic binder may additionally be used to form a paste in which the Au and NiO particles are dispersed uniformly and the paste is then sintered to fabricate a mixed electrode.

If desired, the Au powder may be replaced by a commercial Au paste, which is mixed with a NiO powder and subsequently processed as described above to fabricate a mixed electrode.

In the Au/NiO mixed electrode of the type described above, the $Li_2CO_3$ in the solid electrolyte is anticipated to react with NiO to generate $LiNiO_2$, which in fact has not only high activity on $CO_2$ gas but also high conductivity; therefore, the reaction product $LiNiO_2$ is expected to contribute to better electrode characteristics, as well as stability in the electrode performance.

According to the invention, the NiO powder may be replaced by oxides that are not reactive with Au, such as non-$Al_2O_3$ oxides including $LiAlO_2$, BaO, MgO, SrO and MnO.

The reason for excluding $Al_2O_3$ from the group of applicable oxides that are not reactive with Au is briefly described below. In the present invention, the solid electrolyte is made of a carbonate (such as $Li_2CO_3$, $Na_2CO_3$ or $K_2CO_3$) and the carbonate will react with $Al_2O_3$ to form lithium aluminate according to the following scheme (10):

$$Li_2CO_3 + Al_2O_3 \rightarrow 2LiAlO_2 + CO_2 \qquad (10)$$

This causes a time-dependent change in the electrode, which is no longer capable of maintaining its porous structure.

In contrast, $LiAlO_2$ which is the product of a preliminary reaction between $Li_2CO_3$ and $Al_2O_3$ will cause no unwanted reactions and the electrode is capable of maintaining its porous structure thereby ensure stable performance over an extended period of time.

Other applicable oxides including BaO, MgO, SrO and MnO are capable of forming carbonates, so not only do they fulfill the function of creating a porous structure in the electrode but they are also expected to increase the activity of the electrode on $CO_2$ gas.

The mixed electrode of the design described above ensures that the gas under detection will diffuse smoothly to reach the interface between the electrode and the solid electrolyte, thereby allowing for a smooth progress of the electrode reaction; as a result, the response speed of the sensor is increased and the dynamic range of measurement is expanded without causing time-dependent changes in the characteristic values of the sensor. If the solid electrolyte is made of a selected oxide capable of carbonate formation, the electrode will have an enhanced activity on $CO_2$ gas to thereby exhibit improved response.

Figure 7:
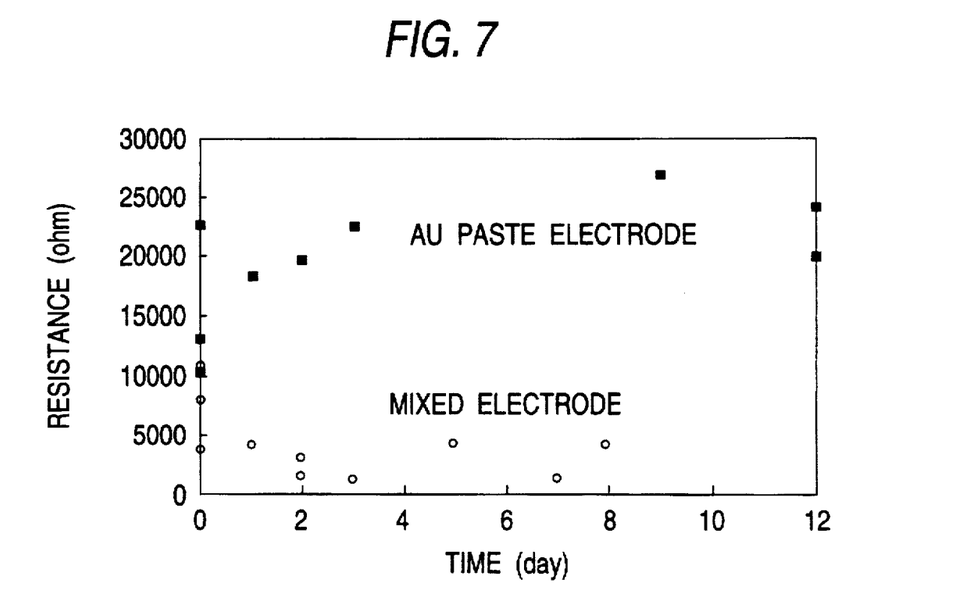
FIG. 7 is a graph comparing the time-dependent change in the mixed electrode of the invention with that of a conventional electrode using a Au paste.

These improvements in the electrode characteristics are observed as a drop in the electrode's interfacial resistance, which leads to a higher response speed of the sensor. It has been confirmed that when measured by a complex impedance method, the interfacial resistance of the mixed electrode of the invention is not only very small (a tenth to a fiftieth of the resistance measured for an electrode using a commercial Au paste) but also less likely to undergo time-dependent changes. FIG. 7 is a graph in which the mixed electrode of the invention and an electrode using a conventional Au paste are compared with each other in terms of the time-dependent change in the interfacial resistance. Obviously, the mixed electrode undergoes smaller time-dependent changes than the Au paste electrode.

If the electrode material of the invention is used in a $CO_2$ gas sensor of a type that employs a solid electrolyte, the electromotive force which is proportional to the $CO_2$ level will follow the Nernst equation on account of the improved response characteristic of the electrode and, in addition, the dynamic range of $CO_2$ level detection is expanded.

As one skilled in the art will readily understand, it goes without saying that the mixed electrode of the invention is applicable not only to a $CO_2$ gas sensor but also to other electrochemical gas sensors for measuring the concentrations of $O_2$, $NO_x$, $SO_x$, CO, etc.

As described above in detail, the solid-electrolyte type gas sensor, that is, the $CO_2$ gas sensor of the invention is the product of an improvement that was made from an entirely different viewpoint than in the conventional art technology. In particular, a lithium containing, mixed transition metal oxide conductor serving as a stable Li source was mixed with a transition metal oxide serving as a basis for the conductor was used as the solid reference electrode and this contributed to improvements not only in the precision of the electromotive force of the $CO_2$ gas sensor but also with respect to the stability of the electromotive force, the time-dependent change in the sensor output, and the response speed of the sensor. In addition, the production cost can be reduced and a smaller apparatus can be manufactured without sacrificing the ease of maintenance. What is more, the sensor of the invention can be operated at lower temperatures than the existing sensors (350° to 400° C. compared with 550° C.), consuming less power and involving a sufficiently reduced thermal load to extend the service life of the sensor. In addition, the solid electrolyte is made of a comparatively water-resistant material and, hence, the sensor of the invention can accomplish consistent detection of the $CO_2$ gas level in gases containing water, water vapor and other aqueous components. The simple design of the invention $CO_2$ gas sensor lends itself to achieving desirable effects such as miniaturization.

Further, as described above, the solid electrolyte is prepared from a complex carbonate containing lithium aluminate as an aggregate and, on account of this, the invention offers the following advantages.

No high temperatures above 800° C. are required during the process of solid electrolyte preparation, so significant cost reduction can be realized in commercial operations and, in addition, solid electrolytes made of a high-density sinter can be prepared at 800° C. and below.

Since lithium aluminate is dispersed in the carbonate to a certain degree of uniformity or a porous body of lithium aluminate is impregnated with the carbonate, the lithium aluminate will serve as an aggregate in the prepared solid electrolyte, thereby increasing its mechanical strength while facilitating its machining.

A sinter made of a metal carbonate alone is insufficient to assure high density but the dispersing of a lithium aluminate powder as an aggregate enables the production of a dense sinter.

Since the solid electrolyte is principally composed of lithium carbonate, $CO_2$ gas sensors using the solid electrolyte have improved moisture resistance.

The $CO_2$ gas sensors fabricated by using the solid electrolyte material having the above features can be operated at 400° C. and below; hence, the power consumption of the heater used in association with the sensing element can be sufficiently reduced to extend the service life of the battery on which the sensor operates. In addition, the improved moisture resistance of the solid electrolyte contributes to a higher reliability of the $CO_2$ gas sensor using it.

Still further, as described above in detail, the present invention is characterized in that a mixture prepared by mixing a Au paste or powder with the powder of NiO or any non-alumina oxide that will not react with Au is used as an electrode material. The mixed electrode prepared from this electrode material can maintain the desired porous structure, so the gas to be detected will diffuse smoothly to reach the interface between the electrode and the electrolyte, thereby allowing for a smooth progress of the electrode reaction. In addition, the mixed electrode retains its micro-structure in a stable manner over an extended period, which helps not only to prevent the decrease in the response speed of the sensor using the electrode but also to improve the stability of its response characteristic.

What is claimed is:

1. A solid-electrolyte gas sensor to measure a $CO_2$ gas level comprising:

a lithium ion conductive solid electrolyte having lithium carbonate with an aluminum containing aggregate, the lithium carbonate being chemically unreactive with the aluminum containing aggregate; and a solid reference electrode combined with the lithium ion conductive solid electrolyte, the solid reference electrode having a lithium containing mixed transition metal oxide conductor which is of the same conduction type as the solid electrolyte;

wherein an electromotive force across the lithium ion conductive solid electrolyte and the solid reference electrode varies according to the $CO_2$ level.

2. The solid-electrolyte gas sensor according to claim 1, wherein the lithium containing mixed transition metal oxide conductor is a compound represented by $Li_xMO_y$ with $0<x\leq1$; $2\leq y\leq12$ and M is a transition metal selected from Co, Ni, Fe, Mn, Ti, V and Cr.

3. The solid-electrolyte gas sensor according to claim 2, wherein the solid reference electrode further includes an oxide of the same transition metal as that of the lithium containing mixed transition metal oxide conductor.

4. The solid-electrolyte gas sensor according to claim 1, wherein the aluminum containing aggregate includes $LiAlO_2$.

5. The solid-electrolyte gas sensor according to claim 1, further comprising a gas permeable electrode formed on an outside surface of the lithium ion conductive solid electrolyte.

6. The solid-electrolyte gas sensor according to claim 5, wherein the gas permeable electrode includes gold.

* * * * *